United States Patent
Penzel et al.

(10) Patent No.: US 6,576,788 B1
(45) Date of Patent: Jun. 10, 2003

(54) METHOD FOR PRODUCING MIXTURES CONSISTING OF DIPHENYLMETHANE DIISOCYANATES AND POLYPHENYLENE-POLYMETHYLENE-POLYISOCYANATES CONTAINING A REDUCED AMOUNT OF CHLORINATED SECONDARY PRODUCTS AND WITH A REDUCED IODINE COLOR INDEX

(75) Inventors: Ulrich Penzel, Tettau (DE); Volker Scharr, Senftenberg (DE); Dieter Starosta, Schwarzheide (DE); Hilmar Boesel, Senftenberg (DE); Eckhard Ströfer, Mannheim (DE); Joachim Pfeffinger, Ludwigshafen (DE); Frank Poplow, Overath (DE); Jürgen Dosch, Ludwigshafen (DE); Hans Volkmar Schwarz, Waterloo (BE); Fritz Näumann, Bensheim (DE); Peter van den Abeel, Kapellen (BE); Jan Jacobs, Hoogerheide (NL); Filip Nevejans, St. Pauwels (BE); Willy van Pee, Brussels (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/673,326

(22) PCT Filed: Apr. 12, 1999

(86) PCT No.: PCT/EP99/02453

§ 371 (c)(1),
(2), (4) Date: Oct. 13, 2000

(87) PCT Pub. No.: WO99/54289

PCT Pub. Date: Oct. 28, 1999

(65) Prior Publication Data (65)

(30) Foreign Application Priority Data

Apr. 21, 1998 (DE) .......................... 198 17 691

(51) Int. Cl.[7] ..................... C07C 249/14; C07C 263/00; C07C 251/00
(52) U.S. Cl. ................. 560/333; 560/331; 560/334; 560/347; 560/352; 560/358; 560/359
(58) Field of Search ................... 560/331, 359, 560/358, 333, 334, 347, 352

(56) References Cited

U.S. PATENT DOCUMENTS

| | | | |
|---|---|---|---|
| 3,226,410 A | * | 12/1965 | Hettich et al. ............... 560/347 |
| 3,381,025 A | * | 4/1968 | Mitsumori et al. ......... 560/347 |
| 3,544,611 A | | 12/1970 | Michelet et al. ............ 560/347 |
| 3,585,229 A | * | 6/1971 | Christian et al. ........... 560/333 |
| 3,969,389 A | * | 7/1976 | Urbach et al. .............. 560/348 |
| 4,289,732 A | | 9/1981 | Bauer et al. |
| 4,419,295 A | | 12/1983 | Hennig et al. |
| 4,465,639 A | * | 8/1984 | Hatfield, Jr. |
| 4,581,174 A | | 4/1986 | Ohlinger et al. |
| 4,851,571 A | | 7/1989 | Sauer et al. |
| 4,876,380 A | | 10/1989 | Chen et al. |
| 5,028,636 A | | 7/1991 | Gebauer et al. ............. 521/131 |
| 5,117,048 A | | 5/1992 | Zaby et al. |
| 5,207,942 A | | 5/1993 | Scherzer et al. ......... 252/182.2 |
| 5,208,368 A | * | 5/1993 | Scherzer et al. ............ 560/333 |
| 5,599,968 A | * | 2/1997 | Bankwitz et al. ........... 560/347 |
| 5,925,783 A | | 7/1999 | Jost et al. |

FOREIGN PATENT DOCUMENTS

| | | |
|---|---|---|
| BE | 790461 | 10/1972 |
| CA | 2180285 | 12/1996 |
| DE | 1792660 | 3/1972 |
| DE | 132340 | 9/1978 |
| DE | 2847243 | 5/1979 |
| DE | 2950216 | 6/1980 |
| DE | 65727 | 12/1982 |
| DE | 3744001 | 6/1989 |
| DE | 285593 | 12/1990 |
| DE | 4006978 | 9/1991 |
| DE | 4021712 | 1/1992 |
| DE | 300168 | 5/1992 |
| DE | 4118914 | 12/1992 |
| DE | 4232769 | 3/1994 |
| DE | 4300774 | 7/1994 |
| DE | 4318018 | 12/1994 |
| EP | 150435 | 8/1985 |
| EP | 291819 | 11/1988 |
| EP | 445602 | 9/1991 |
| EP | 751118 | 1/1997 |
| FR | 2325637 | 4/1977 |
| GB | 1238669 | 7/1971 |
| GB | 1341311 | 12/1973 |
| GB | 1549294 | 7/1979 |
| JP | 07/082230 | 9/1993 |
| WO | WO 96/16028 | 5/1996 |

OTHER PUBLICATIONS

Derwent Abstract of JP 07/082230.
Derwent Abstract of DD 300168.
Derwent Abstract of DD 132340.
Derwent Abstract of DE 4318018.
Derwent Abstract of DE 4006978.
Derwent Abstract of DE 4,118,914.
Derwent Abstract of DE 4232769.
Derwent Abstract of DE 4300774.
Derwent Abstract of DD 285,593.
Derwent Abstract of FR 2325637.

* cited by examiner

Primary Examiner—Alan L. Rotman
Assistant Examiner—Taylor V. Oh
(74) Attorney, Agent, or Firm—Fernando A. Borrego

(57) ABSTRACT

In a process for preparing mixtures of diphenylmethane diisocyanates and polyphenylpolymethylene polyisocyanates having a reduced content of chlorinated by-products and a reduced iodine color number by two-stage reaction of the corresponding mixtures of diphenylmethanediamines and polyphenylpolymethylenepolyamines with phosgene in the presence of at least one inert organic solvent at elevated temperature, separation of the excess phosgene and solvent after the phosgenation is complete and thermal treatment of the reaction product, the mass ratios of phosgene to hydrogen chloride in the residence time apparatus of the second stage of the phosgenation are at the same time 10–30:1 in the liquid phase and 1–10:1 in the gas phase.

14 Claims, No Drawings

METHOD FOR PRODUCING MIXTURES CONSISTING OF DIPHENYLMETHANE DIISOCYANATES AND POLYPHENYLENE-POLYMETHYLENE-POLYISOCYANATES CONTAINING A REDUCED AMOUNT OF CHLORINATED SECONDARY PRODUCTS AND WITH A REDUCED IODINE COLOR INDEX

The present invention relates to a process for preparing mixtures of diphenylmethane diisocyanates and polyphenylpolymethylene polyisocyanates, known as PMDI, having a reduced content of chlorinated by-products and a reduced iodine color number by two-stage reaction of the corresponding mixtures of diphenylmethanediamines and polyphenylpolymethylenepolyamines, known as PMDA, with phosgene in the presence of at least one inert organic solvent, where the corresponding carbamoyl chlorides formed in the first stage of the phosgenation and the amine hydrochlorides in the second stage of the phosgenation run through a residence time apparatus in which the amine hydrochlorides are phosgenated to the corresponding carbamoyl chlorides and the carbamoyl chlorides are dissociated into the corresponding isocyanates and hydrogen chloride and the mass ratios of phosgene to hydrogen chloride are at the same time 10–30:1 in the liquid phase and 1–10:1 in the gas phase.

PMDI is the industrially most important isocyanate for producing rigid polyurethane foams which are preferably used as insulation material in the building industry, as insulating foam in the refrigeration appliance industry and as sandwich construction material. Usually, part of the diphenylmethane 4,4'-diisocyanate, known as MMDI, present in the PMDI is recovered by means of a suitable technological operation such as distillation or crystallization. MMDI is in turn an important constituent of polyurethane formulations for compact, microcellular and cellular polyurethanes such as adhesives, coatings, fibers, elastomers and integral foams. Accordingly, the term "PMDI" used in the present text also encompasses PMDI mixtures in which monomeric MDI, for example 4,4'-, 2,2'- and/or 2,4'-MDI, is present.

PMDI is, as is known, prepared by phosgenation of the corresponding PMDA in the presence of an inert organic solvent. PMDA is in turn obtained by means of an acid aniline-formaldehyde condensation which can be carried out industrially either continuously or batchwise. The proportions of diphenylmethanediamines and the homologous polyphenylpolymethylenepolyamines and their positional isomerism in the PMDA are controlled by selection of the ratios of aniline, formaldehyde and acid catalyst and also by means of a suitable temperature and residence time profile. High contents of 4,4'-diphenylmethanediamine together with a simultaneously low proportion of the 2,4' isomer of diphenylmethanediamine are obtained on an industrial scale by the use of strong mineral acids such as hydrochloric acid as catalyst in the aniline-formaldehyde condensation.

All the acid aniline-formaldehyde condensation processes described in the specialist and patent literature have in common the formation of undesired by-products, for example the formation of N-methylated and N-formylated compounds and also the formation of dihydroquinazolines. In addition, industrial PMDAs can contain residual amounts of unrearranged aminobenzylanilines which can in turn be a further starting point for further reactions. Another disadvantage is that the acid aniline-formaldehyde condensation forms chromophores which discolor the PMDA. These discolorations are reduced only insufficiently, if at all, in the subsequent neutralization of the acid condensation catalyst and the removal of the aniline used in excess in the condensation; the same applies to the subsequent process steps of the PMDI preparation.

In the phosgenation step, the PMDA is reacted with phosgene in an inert organic solvent to form PMDI. The undesired by-products and chromophores in the PMDA can react with phosgene to form further compounds such as secondary carbamoyl chlorides and products of chlorination of the aromatic ring and/or at the methylene bridge. In addition, the phosgenation step forms further chlorine-containing by-products such as allophanoyl chlorides and isonitrile dichlorides. The chlorine-containing compounds and chromophores are incorporated both into the low molecular weight fraction whose central constituent is the diphenylmethane diisocyanate and also into the oligomeric fractions of polyphenylpolymethylene polyisocyanate.

The technological operations which follow the phosgenation, namely removal of the phosgene used in excess, the removal of the inert solvent, the thermal treatment, the so-called dechlorination and the removal of part of the MMDI present in the crude PMDI by distillation and/or crystallization, do not lastingly reduce the content of chlorine-containing compounds and the discoloration of the crude PMDI increases with continuing, especially thermal, stressing of the product.

Chlorine-containing and/or discolored PMDI is undesirable in further processing to form polyisocyanate-polyalcohol polyaddition plastics. In particular, chlorine-containing compounds which can readily form ionic chloride, as determined by the ASTM D 1638-74 method, can cause considerable interference in the blowing reaction of foam production by forming salts with the blowing catalyst. Undesirable discolorations of the PMDI also show up in the plastics prepared therefrom. Although the color of the polyisocyanate-polyalcohol polyaddition plastics does not have an adverse effect on their mechanical properties, light-colored products are preferred because of their good versatility in the production process of the processor, e.g. the ability of light to pass through thin covering layers and the ability to produce a variety of colors.

There have therefore been many attempts to reduce the content of chlorinated by-products and the discoloration of PMDI in mixtures with MMDI.

According to GB 1 549 294, addition of isoureas in an amount of 25–250 mol % can reduce the ASTM D 1638-74 acidity of the PMDI. A disadvantage of this method is that an additional agent has to be used and the lowering of the acidity is only partially successful.

DD 285 593 proposes treating PMDI with acid amides in an amount of 0.01–0.2% at 100–140° C. for 0.2–6 hours. After the treatment, the hydrogen chloride formed is driven off by stripping with nitrogen or solvent vapors. Disadvantages of this process are the insufficient effect of the acid amides, the formation of additional constituents in the PMDI as a result of the unavoidable secondary reaction of the isocyanates with the acid amides to form acylated ureas and the outlay in terms of apparatus for treating the PMDI with the acid amides and for stripping out the hydrogen chloride, both that added as catalyst and that which is formed.

DE 2 847 243 proposes removal of phosgene by stripping with gaseous hydrogen chloride or nitrogen at 170° C. for 2 hours. A disadvantage is the considerable amounts of gases laden with phosgene or with phosgene/hydrogen chloride which make an additional outlay for the subsequent materials separation or an additional outlay for the neutralization of the acidic gas constituents absolutely necessary. The additional disadvantage of the process described in DE 2 847 243, namely the long residence time for stripping, is partially alleviated in JP 07 233 136 A by two-stage stripping with hydrogen chloride after phosgene removal at 115° C./30 minutes and 160° C./3 minutes. However, this results in the disadvantage of an additional technological operation and an again significant gas stream which requires treatment.

According to JP 07 082 230 A, organic phosphites are added to the aniline before the aniline-formaldehyde condensation.

To lower the iodine color number, the addition of numerous compounds after the phosgenation has been proposed: water (U.S. Pat. No. 4,465,639), phenol derivatives (DE 4 300 774), amines and/or ureas (DE 4 232 769), acid chlorides/chloroformates (DE 4 118 914), polyoxyalkylene polyalcohols (DE 4 021 712), dialkyl or trialkyl phosphites (DE 4 006 978), low molecular weight monohydric or polyhydric alcohols (EP 445 602), acid chlorides/antioxidant (DE 4 318 018).

All processes which propose the addition of compounds to raw materials or products of a preparation stage for PMDI have the disadvantage of the addition of an additional agent with the inherent danger of its corrosive action on the equipment components and the formation of by-products from precisely these added agents, which by-products can in turn have an adverse effect on the product or the equipment.

U.S. Pat. No. 4,876,380 proposes lightening the color by extraction of a chromophore-rich PMDI fraction from the PMDI by means of pentane/hexane. Disadvantages of this process are the carrying-out of a complicated technological operation with additional steps for working up the extractant and the unavoidable formation of a reduced-quality PMDI fraction for which applications that use up equivalent amounts have to be found.

It is an object of the present invention to reduce the content of chlorinated by-products and the iodine color number of the PMDI in admixture with MMDI while avoiding the abovementioned disadvantages. In particular, the addition of auxiliaries and/or the use of additional apparatuses should not be necessary.

We have found that this object is achieved by two-stage reaction of the corresponding mixtures comprising diphenylmethanediamines and polyphenylpolymethylenepolyamines with phosgene in the presence of at least one inert organic solvent, where the corresponding carbamoyl chlorides formed in the first stage of the phosgenation and the amine hydrochlorides in the second stage of the phosgenation run through a residence time apparatus in which the amine hydrochlorides are phosgenated to the corresponding carbamoyl chlorides and the carbamoyl chlorides are dissociated into the corresponding isocyanates and hydrogen chloride and the mass ratios of phosgene to hydrogen chloride are at the same time 10–30:1 in the liquid phase and 1–10:1 in the gas phase.

The present invention accordingly provides a process for preparing mixtures comprising diphenylmethane diisocyanates and polyphenylpolymethylene polyisocyanates having a reduced content of chlorinated by-products and a reduced iodine color number by two-stage reaction of the corresponding mixtures comprising diphenylmethanediamines and polyphenylpolymethylenepolyamines with phosgene in the presence of at least one inert organic solvent, wherein the corresponding carbamoyl chlorides formed in the first stage of the phosgenation and the amine hydrochlorides in the second stage of the phosgenation run through a residence time apparatus in which the amine hydrochlorides are phosgenated to the corresponding carbamoyl chlorides and the carbamoyl chlorides are dissociated into the corresponding isocyanates and hydrogen chloride and the mass ratios of phosgene to hydrogen chloride are at the same time 10–30:1 in the liquid phase and 1–10:1 in the gas phase.

The phosgenation of primary amines in a mixing reactor as first stage of the phosgenation has been described a number of times. Thus, for example, U.S. Pat. No. 3,544,611 and EP A2-0150435 report the phosgenation in a pressure mixing circuit. Furthermore, EP A2-0291819 discloses carrying out this reaction in a reaction pump. Many different designs of static mixers have been described, for example: annular slot nozzle (FR 2 325 637, DE 1 792 660), ring-eye nozzle (DE 3 744 001), flat jet nozzle (EP A1-0 065 727), fan jet nozzle (DE 2 950 216), angle-jet chamber nozzle (DD 300 168), three-fluid nozzle (DD 132 340).

It is known per se that the corresponding carbamoyl chlorides and amine hydrochlorides formed in the first stage of the phosgenation can be run through a residence time apparatus in which the amine hydrochlorides are phosgenated to form the corresponding carbamoyl chlorides and the carbamoyl chlorides are dissociated into the corresponding isocyanates and hydrogen chloride. The isocyanate prepared according to WO 96/16 028 in a tube reactor at 80–150° C. has a very unsatisfactory hydrolyzable chlorine content of max. 2% and makes PMDI prepared by this process unusable for most applications. In BE 790 461 and BE 855 235, stirred apparatuses are used as residence time reactors. U.S. Pat. No. 3,544,611 describes a distillation residence time apparatus operating at 10–50 bar and 120–150° C. and having an "elongated distillation zone" for dissociating the carbamoyl chlorides and removing the hydrogen chloride. DE 3 744 001 proposes a perforated plate column through which the reaction mixture flows from the bottom upward and which has more than 10 perforated plates, a residence time of max. 120 minutes and liquid velocities of 0.05–4 m/s and gas velocities of 2–20 m/s. Disadvantages of the prior art are the drastic conditions in the residence time apparatuses and the relatively long residence time of the crude PMDI formed. Experience indicates that the prior art allows only a very unsatisfactory quality level in respect of the color and the chlorine content of the PMDI.

The combination of mixing and residence time apparatuses for preparing PMDI, in particular for the two-stage phosgenation, is also known. Thus, in DE 3 744 001, a ring-eye nozzle as reactor for reacting primary amines with phosgene in an inert solvent to give the corresponding carbamoyl chlorides and amine hydrochlorides is combined with one or more perforated plate columns as apparatus for phosgenating the amine hydrochlorides and dissociating the carbamoyl chlorides. In U.S. Pat. No. 3,381,025, the first stage is carried out at <60° C. in an inert solvent having a boiling point of 100–190° C. and the reaction product is transferred to a second stage in which the temperature is held at such a level above the boiling point of the inert solvent that the ratio of escaping phosgene to inert solvent is greater than two and, if desired, phosgene is additionally fed into the second reaction stage. Disadvantages are the high outlay in terms of apparatus and the high energy consumption in the second stage of the phosgenation as residence time apparatus or for condensing the gaseous mixture of phosgene/inert solvent. Experience indicates that the prior art allows only a very unsatisfactory quality level in respect of the chlorine content and the color of the PMDI.

It is therefore a further object of the present invention to reduce the content of chlorinated by-products and the iodine color number of PMDI using technological equipment which is simpler in terms of safety and apparatus.

We have found that this object is achieved by two-stage reaction of PMDA with phosgene in the presence of at least one inert organic solvent, where the first stage of the phosgenation is carried out in a static mixer and the second stage of the phosgenation is carried out in a residence time apparatus and the mass ratios of phosgene to hydrogen chloride in the residence time apparatus are at the same time 10–30:1 in the liquid phase and 1–10:1 in the gas phase.

Static mixers employed for the first stage of the phosgenation are the known and abovementioned pieces of equipment, in particular nozzles. The temperature in the first stage of the phosgenation is usually from 40 to 150° C., preferably from 60 to 130° C., particularly preferably 90–120° C.

The mixture from the first stage of the phosgenation is fed to a column in which, according to the present invention, the mass ratios of phosgene to hydrogen chloride in the second stage of the phosgenation are at the same time 10–30:1 in the liquid phase and 1–10:1 in the gas phase.

It is particularly advantageous to operate the column in countercurrent. The product mixture from the first stage of the phosgenation is preferably fed into the column such that the PMDI/solvent/phosgene mixture leaves the column at the bottom and a phosgene/hydrogen chloride mixture is taken off at the top of the column and is fed to the hydrogen chloride/phosgene separation. The temperature at which the mixture from the first stage of the phosgenation enters the column is preferably 80–120° C., particularly preferably 82–117° C. The temperature at the bottom of the column is preferably 80–120° C., particularly preferably 90–110° C. The pressure at the top of the column is preferably 1.0–4.7 atm (gauge pressure), particularly preferably 2.0–3.7 atm (gauge pressure). The hydrogen chloride/phosgene ratio in the column is set and controlled by means of the excess of phosgene in the first stage of the phosgenation, the temperature at which the reaction product enters the column, the column pressure and the temperature at the bottom of the column. The phosgene can all be fed into the first stage of the phosgenation or only part of it can be introduced into the first stage. In the latter case, a further amount of phosgene is fed into the residence time apparatus of the second stage of the phosgenation. The column used preferably has <10 theoretical plates. The use of a valve tray column is advantageous. It is also possible to use other internal column fittings which ensure the necessary residence time for the carbamoyl chloride dissociation and rapid and effective removal of hydrogen chloride, for example bubble cap tray columns or distillation trays having relatively high liquid weirs. The perforated plate column proposed in DE-A 3 744 001 is very unsatisfactory in industry for the task of mild carbamoyl chloride dissociation together with rapid and effective hydrogen chloride removal and is unsuitable as residence time apparatus for preparing a PMDI having a reduced chlorine content and a reduced iodine color number because of its cocurrent principle which inevitably leads to large liquid holdups and to greater difficulty in achieving rapid removal of hydrogen chloride.

The mixtures of diphenylmethane diisocyanates and polyphenylpolymethylene polyisocyanates prepared by the process of the present invention usually have a diphenylmethane diisocyanate isomer content of from 30 to 90% by mass, preferably from 30 to 70% by weight, an NCO content of from 29 to 33% by weight, preferably from 30 to 32% by mass, based on the weight of crude MDI, and a viscosity, determined at 25° C. in accordance with DIN 51550, of not more than 2500 mPa.s, preferably from 40 to 2000 mPa.s.

Crude MDIs having such isomer and homologue compositions can be prepared by phosgenation of crude MDAs having corresponding product compositions in the presence of at least one inert organic solvent.

Suitable crude MDAs are advantageously obtained by condensation of aniline and formaldehyde in a molar ratio of 6–1.6:1, preferably 4–1.9:1, and a molar ratio of aniline to acid catalysts of 1:0.98–0.01, preferably 1:0.8–0.1.

The formaldehyde is preferably used in the form of an aqueous solution, e.g. as a commercial 30–50% strength by mass solution.

Acid catalysts which have been found to be useful are proton donors such as acid ion exchange resins or strong organic and preferably inorganic acids. For the purposes of the present invention, strong acids are those having a pKa of less than 1.5; in the case of polybasic acids, this value is that for the first hydrogen dissociation. Examples which may be mentioned are hydrochloric acid, sulfuric acid, phosphoric acid, fluorosulfonic acid and oxalic acid. Hydrogen chloride in gaseous form can also be used. Preference is given to using aqueous hydrochloric acid in concentrations of from about 25 to 33% by mass.

Suitable processes for preparing crude MDA are described, for example, in CA-A-700 026, DE-B-22 27 110 (U.S. Pat. No. 4,025,557), DE-B-22 38 920 (U.S. Pat. No. 3,996,283), DE-B-24 26 116 (GB-A-1,450,632), DE-A-12, 42,623 (U.S. Pat. No. 3,478,099), GB-A-1,064,559 and DE-A-32 25 125.

The other starting component for preparing crude MDI is phosgene. The gaseous phosgene can be used as such or diluted with gases which are inert under the reaction conditions, e.g. nitrogen, carbon monoxide, etc. The molar ratio of crude MDA to phosgene is advantageously selected such that from 1 to 10 mol, preferably from 1.3 to 4 mol, of phosgene are present in the reaction mixture per mole of $NH_2$ groups. The phosgene can all be fed into the first stage of the phosgenation or part of it can also be added to the residence time apparatus of the second stage of the phosgenation.

Suitable inert organic solvents are compounds in which the crude MDA and the phosgene are at least partially soluble.

Solvents which have been found to be useful are chlorinated, aromatic hydrocarbons, for example monochlorobenzene, dichlorobenzenes such as o-dichlorobenzene and p-dichlorobenzene, trichlorobenzenes, the corresponding toluenes and xylenes, chloroethylbenzene, monochlorobiphenyl, alpha- or beta-naphthyl chloride and dialkyl phthalates such as diethyl isophthalate. Particular preference is given to using monochlorobenzene, dichlorobenzenes or mixtures of these chlorobenzenes as inert organic solvents. The solvents can be used individually or as mixtures. It is advantageous to use a solvent which has a boiling point lower than that of the MDI isomers so that the solvent can easily be separated from the crude MDI by distillation. The amount of solvent is advantageously selected such that the reaction mixture has an isocyanate content of from 2 to 40% by mass, preferably from 5 to 20% by mass, based on the total weight of the reaction mixture.

The crude MDA can be employed as such or as a solution in organic solvents. However, particular preference is given to using crude MDA solutions having an amine content of from 2 to 45% by mass, preferably from 25 to 44% by mass, based on the total weight of the amine solution.

Subsequent to the phosgenation, the excess phosgene, the hydrogen chloride and the solvent are preferably separated from the reaction product. To prepare a PMDI having a reduced content of chlorinated by-products and a reduced iodine color number, it is particularly advantageous for the residual content of phosgene after the phosgene removal to be <10 ppm of phosgene. These work-up steps are carried out by generally known methods. The two-ring isomers can be separated from the MDI mixture by known methods such as distillation or crystallization.

The product is then usually stabilized using an antioxidant based on sterically hindered phenols and/or at least one aryl phosphite. The stabilizers are advantageously used in an amount of up to max. 1% by mass, preferably from 0.001 to 0.2% by mass. Examples of suitable antioxidants based on sterically hindered phenols are: styrenized phenols, i.e. phenols which have a 1-phenylethyl group bound in the 2 or 4 position or in the 2 and 4 and/or 6 positions, bis(2-hydroxy-5-methyl-3-tert-butylphenyl)methane, 2,2-bis(4-hydroxyphenyl)propane, 4,4,'-dihydroxybiphenyl, 3,3'-dialkyl- or 3,3 ', 5,5'-tetraalkyl-4,4'-dihydroxybiphenyl, bis (4-hydroxy-2-methyl-5-tert-butylphenyl)sulfide, hydroquinone, 4-methoxy-, 4-tert-butoxy- or 4-benzyloxyphenol, mixtures of 4-methoxy-2- or -3-tert-butylphenol, 2,5-dihydroxy-1-tert-butylbenzene, 2,5-dihydroxy-1,4-di-tert-butylbenzene, 4-methoxy-2,6-di-tert-butylphenol and preferably 2,6-di-tert-butyl-p-cresol.

Aryl phosphites which have been found to be useful are tri(alkylphenyl)phosphites having from 1 to 10 carbon atoms in the alkyl radical, e.g. tri(methylphenyl)phosphite, tri (ethylphenyl)phosphite, tri(n-propylphenyl)phosphite, tri (isopropylphenyl)phosphite, tri(n-butylphenyl)phosphite, tri (sec-butylphenyl)phosphite, tri(tert-butylphenyl)phosphite, tri(pentylphenyl)phosphite, tri(hexylphenyl)phosphite, tri (2-ethylhexylphenyl)phosphite, tri(octylphenyl)phosphite, tri(2-ethyloctylphenyl)phosphite, tri(decylphenyl)phosphite and preferably tri(nonylphenyl)phosphite, and in particular triphenyl phosphite.

The present invention also provides a process for preparing 2,2'-, 2,4'- and/or 4,4'-MDI from the mixture comprising diphenylmethane diisocyanate and polyphenylpolymethylene polyisocyanate prepared according to the present invention, which comprises separating 2,2'-, 2,4'- and/or 4,4'-MDI, preferably 4,4'-MDI, by distillation and/or crystallization from the mixtures prepared according to the present invention.

Accordingly, the crude PMDIs prepared in this way are usually subjected to a thermal after-treatment which can be coupled with the separation of the MMDI isomers. For this purpose, the PMDI is heated to 170–230° C., preferably 180–220° C., and treated at this temperature at a pressure of from 0.01 to 100 mbar, preferably from 0.1 to 20 mbar, for at least 5 minutes and in particular from 5 to 45 minutes, if desired while passing in an amount of at most 5 standard m$^3$/t of PMDI of an inert gas such as nitrogen, preferably at most 0.5 standard m$^3$/t of PMDI of inert gas.

After cooling to 30–60° C., the PMDI is usually passed to intermediate storage.

The invention is illustrated by the examples below:

EXAMPLE 1

The phosgenation is carried out using a PMDA having the following composition:

| | |
|---|---|
| viscosity at 70° C. | 348 mm$^2$/s |
| 4,4'-diphenylmethanediamine (4,4'-MDA) content | 44.6% by mass |
| MDA content | 52% by mass |
| 3-ring-PMDA content | 23% by mass |

| -continued | |
|---|---|
| N-methyl-MDA content | 0.14% by mass |
| N-formyl-MDA content | 1194 ppm. |

3840 kg/h of such a PMDA as a 38.7% strength by mass solution in monochlorobenzene (MCB) are phosgenated with 26,400 kg/h of a 42% strength by mass solution of phosgene in MCB in an angle-jet chamber nozzle. The reaction mixture heats up to 118° C. in the reactor of the first stage of the phosgenation as a result of the exothermic reaction of PMDA with phosgene and is at 92° C. on entry into a valve tray column having 6 theoretical plates in the stripper section and 2 plates in the enrichment section. The column is operated at a pressure of 4.3 bar (abs.) and the composition of the bottoms is adjusted by means of the amount of steam used for heating so that the phosgene content at the bottom of the column is about 10% by mass, which corresponds to a temperature at the bottom of the column of 95–97° C. The mass ratios of phosgene to hydrogen chloride are 14.2:1 at the bottom of the column and 1.6:1 at the top of the column. The hydrogen chloride formed in the first stage of the phosgenation and liberated in the column from the dissociation of the carbamoyl chlorides is, together with part of the phosgene used in excess, taken off at the top at 91° C. To prevent entrainment of PMDI droplets in the hydrogen chloride and phosgene gas streams, 1350 kg/h of MCB are additionally fed in at the top of the column.

The mixture leaving the phosgenation is freed of phosgene and MCB and thermally after-treated in accordance with the prior art.

The PMDI prepared in this way has the following product properties:

| | |
|---|---|
| viscosity at 25° C. in accordance with DIN 51550 | 182 mPa · s |
| isocyanate group content in accordance with ASTM D 1638-74 | 31.5% by mass |
| acidity in accordance with ASTM D 1638-74 | 56 ppm HCl |
| total chlorine in accordance with DIN 35474 | 900 ppm HCl |
| iodine color number[1] | 9.7 |

[1]Measured using a three-filter instrument, e.g. LICO 200 (Dr. Lange)

Comparative Example 1

For comparison, the same PMDA as in Example 1 is phosgenated in the same angle-jet chamber nozzle and the same column. 3840 kg/h of this PMDA as a 38.7% strength by mass solution in monochlorobenzene (MCB) are likewise reacted with 26,400 kg/h of a 42% strength by mass solution of phosgene in MCB. Likewise, 1350 kg/h of MCB are additionally fed in at the top of the column.

The entry temperature of the PMDA/MCB stream into the angle-jet chamber nozzle is selected so that the temperature of the reaction mixture leaving the nozzle is 96° C. The reaction mixture is at 78° C. on entry into the valve tray column. The column is operated at a top pressure of 5.2 bar (abs.). At a bottom temperature set to 116° C., a temperature at the top of 76° C. is established. The mass ratios of phosgene to hydrogen chloride are 9.2:1 at the bottom of the column and 0.95:1 at the top of the column.

The PMDI prepared as a comparision has the following product properties:

| | |
|---|---|
| viscosity at 25° C. in accordance with DIN 51550 | 197 mPa · s |
| isocyanate group content in accordance with ASTM D 1638-74 | 31.8% by mass |
| acidity in accordance with ASTM D 1638-74 | 197 ppm HCl |
| total chlorine in accordance with DIN 35474 | 1900 ppm HCl |
| iodine color number[1] | 15 |

We claim:

1. A process for preparing mixtures comprising diphenylmethane diisocyanates and polyphenylpolymethylene polyisocyanates having a reduced content of chlorinated by-products and a reduced iodine color number, said process comprising reacting diphenylmethanediamines and polyphenylpolymethylenepolyamines (PMDA) with phosgene in the presence of at least one inert organic solvent in a two-stage reaction comprising first and second phosgenation stages, wherein the mass ratios of said phosgene to hydrogen chloride in a residence time apparatus of the second phosgenation stage are at the same time 10–30:1 in the liquid phase and 1–10:1 in the gas phase.

2. A process as claimed in claim 1, wherein the first phosgenation state comprises using a static mixer having a mix exit temperature of 80–120° C.

3. A process as claimed in claim 1, wherein the second phosgenation stage comprises using a column having <10 theoretical plates.

4. A process as claimed in claim 3, wherein the column is operated in countercurrent fashion.

5. A process as claimed in claim 3, wherein the column is a valve tray column.

6. A process as claimed in claim 3, wherein the column is a bubble cap tray column.

7. A process as claimed in claim 3, wherein the column has distillation trays having relatively high liquid weirs.

8. A process as claimed in claim 2, wherein the PMDA concentration in the inert solvent in the stream to the static mixer is at most 44% by mass.

9. A process as claimed in claim 3, wherein the temperature at which the mixture from the first phosgenation stage enters the column is 80–120° C.

10. A process as claimed in claim 3, wherein the temperature at the bottom of the column is 80–120° C.

11. A process as claimed in claim 3, wherein the pressure at the top of the column is 1.0–4.7 atm (gauge pressure).

12. A process as claimed in claim 9, wherein the temperature at which the mixture from the first phosgenation stage enters the column is 82–117° C.

13. A process as claimed in claim 10, wherein the temperature at the bottom of the column is 90–110° C.

14. A process as claimed in claim 11, wherein the pressure at the top of the column is 2.0–3.7 atm (gauge pressure).

\* \* \* \* \*